United States Patent
May et al.

(10) Patent No.: US 9,204,886 B2
(45) Date of Patent: Dec. 8, 2015

(54) THREADED, FLEXIBLE IMPLANT AND METHOD FOR THREADING A CURVED HOLE

(75) Inventors: Justin J. May, Leesburg, IN (US); Andrew J. Steiner, Warsaw, IN (US)

(73) Assignee: Zimmer, Inc., Warsaw, IN (US)

( * ) Notice: Subject to any disclaimer, the term of this patent is extended or adjusted under 35 U.S.C. 154(b) by 914 days.

(21) Appl. No.: 12/466,724

(22) Filed: May 15, 2009

(65) Prior Publication Data

US 2010/0292695 A1 Nov. 18, 2010

(51) Int. Cl.
*A61B 17/72* (2006.01)
*A61B 17/16* (2006.01)
*A61B 17/74* (2006.01)

(52) U.S. Cl.
CPC ......... *A61B 17/1642* (2013.01); *A61B 17/1655* (2013.01); *A61B 17/1668* (2013.01); *A61B 17/744* (2013.01)

(58) Field of Classification Search
CPC ........... A61B 17/1642; A61B 17/1655; A61B 17/1668; A61B 17/744
USPC ..................................... 606/62–68, 246–279
See application file for complete search history.

(56) References Cited

U.S. PATENT DOCUMENTS

| | | | |
|---|---|---|---|
| 3,051,169 A | 8/1962 | Grath | |
| 4,259,072 A * | 3/1981 | Hirabayashi et al. | 433/173 |
| 4,711,232 A | 12/1987 | Fischer et al. | |
| 4,760,843 A | 8/1988 | Fischer et al. | |
| 4,762,453 A | 8/1988 | DeCaro | |
| 4,790,303 A | 12/1988 | Steffee | |
| 4,947,502 A | 8/1990 | Engelhardt | |
| 4,978,350 A * | 12/1990 | Wagenknecht | 606/312 |
| 5,013,314 A | 5/1991 | Firica et al. | |
| 5,017,057 A | 5/1991 | Kryger | |
| 5,026,373 A | 6/1991 | Ray et al. | |
| 5,167,582 A | 12/1992 | Hunt | |
| 5,527,316 A | 6/1996 | Stone et al. | |
| 5,645,545 A * | 7/1997 | Bryant | 606/62 |
| 5,827,289 A | 10/1998 | Reiley et al. | |
| 5,921,728 A | 7/1999 | Kammeraad et al. | |
| 6,053,922 A | 4/2000 | Krause et al. | |
| 6,077,265 A * | 6/2000 | Werding et al. | 606/67 |

(Continued)

FOREIGN PATENT DOCUMENTS

| | | |
|---|---|---|
| DE | 10360076B3 B3 | 4/2005 |
| FR | 2697990A3 A3 | 5/1994 |

OTHER PUBLICATIONS

Product Brochure—Zimmer Trabecular Metal Osteonecrosis Intervention Implant System, Zimmer 2005, 2 pages (Osteonecrosis1).

(Continued)

*Primary Examiner* — Jerry Cumberledge
*Assistant Examiner* — Nicholas Plionis
(74) *Attorney, Agent, or Firm* — Schwegman Lundberg & Woessner, P.A.

(57) ABSTRACT

An apparatus and method for threading a curved hole and inserting a threaded, flexible implant into the same. A threaded, flexible implant, which includes a flexible shaft and external thread, is provided to facilitate fixation in a curved, threaded hole. The threaded, flexible implant has a variable thread pitch from the concave to the convex surface thereof, and the curved, threaded hole has corresponding thread pitches.

19 Claims, 5 Drawing Sheets

(56) References Cited

U.S. PATENT DOCUMENTS

| | | | |
|---|---|---|---|
| 6,245,112 B1* | 6/2001 | Doubler et al. | 623/22.41 |
| 6,306,140 B1* | 10/2001 | Siddiqui | 606/315 |
| 6,447,514 B1 | 9/2002 | Stalcup et al. | |
| 6,790,210 B1 | 9/2004 | Cragg et al. | |
| 7,258,692 B2 | 8/2007 | Thelen et al. | |
| 7,377,921 B2 | 5/2008 | Studer et al. | |
| 2003/0055428 A1* | 3/2003 | Swanson | 606/62 |
| 2005/0177167 A1 | 8/2005 | Muckter | |
| 2005/0283239 A1* | 12/2005 | Crozet | 623/17.11 |
| 2006/0004465 A1* | 1/2006 | Bergin et al. | 623/23.31 |
| 2006/0009855 A1 | 1/2006 | Goble et al. | |
| 2006/0064164 A1 | 3/2006 | Thelen | |
| 2006/0129147 A1 | 6/2006 | Biedermann et al. | |
| 2006/0264951 A1 | 11/2006 | Nelson et al. | |
| 2007/0083265 A1* | 4/2007 | Malone | 623/17.11 |
| 2007/0135841 A1* | 6/2007 | Dreyfuss | 606/232 |
| 2007/0225721 A1 | 9/2007 | Thelen et al. | |
| 2007/0288022 A1* | 12/2007 | Lutz | 606/69 |
| 2008/0004626 A1 | 1/2008 | Glazer et al. | |
| 2008/0039941 A1* | 2/2008 | Steinberg | 623/16.11 |
| 2008/0097398 A1* | 4/2008 | Mitelberg et al. | 604/525 |
| 2008/0183220 A1 | 7/2008 | Glazer et al. | |
| 2008/0195096 A1 | 8/2008 | Frei | |
| 2008/0221620 A1* | 9/2008 | Krause | 606/255 |
| 2009/0118771 A1* | 5/2009 | Gonzalez-Hernandez | 606/286 |
| 2011/0144703 A1* | 6/2011 | Krause et al. | 606/309 |
| 2012/0232597 A1* | 9/2012 | Saidha et al. | 606/305 |

OTHER PUBLICATIONS

Surgical Technique—Zimmer Trabecular Metal Osteonecrosis Intervention Implant System, Zimmer 2005, 4 pages (Osteonecrosis2).

* cited by examiner

FIG._2

THREADED, FLEXIBLE IMPLANT AND METHOD FOR THREADING A CURVED HOLE

BACKGROUND

1. Field of the Invention

The present invention relates to bone implants and methods for implanting them. More specifically, the invention relates to a threaded, flexible implant and method for threading a curved hole.

2. Description of the Related Art

Various methods and apparatuses have been developed for joining bone fragments of a fractured bone. One such method is utilized in a fractured femoral neck. This method includes the use of a side plate/hip screw combination, i.e., a bone plate affixed to a lateral aspect of the femur and having a lag screw operably connected thereto, with the lag screw extending into the femoral head. Another method used to treat a fractured femoral neck utilizes an intramedullary rod to support a lag screw, rather than a side plate. Various other bone fixation and anchoring methods and devices are known, including various fixation pins or screws which can be implanted in the various bones of the body.

SUMMARY

An apparatus and method are provided for threading a curved hole in a bone and inserting a threaded, flexible implant into the same. A threaded, flexible implant, which includes a flexible shaft and external thread, is provided to facilitate fixation in a curved, threaded hole. The threaded, flexible implant has a variable thread pitch from the concave to the convex surface thereof, and the curved, threaded hole has corresponding thread pitches. In certain embodiments, the threaded, flexible implant includes a reamer connected to an end thereof. In this embodiment, the reamer may be utilized to form a hole in a bone while the combination of the external thread and at least one flute effects tapping of the hole formed by the reamer end of the flexible implant. In certain embodiments, the implant may remain in place in the bone to provide an anchor to another implant structure and/or to reduce a fracture, for example; or may be removed in favor of a second, threaded, flexible implant.

The invention, in one form thereof, comprises a threaded, flexible implant including a biocompatible flexible shaft having a longitudinal axis and an external thread protruding radially from the flexible shaft helically about the longitudinal axis. The external thread of this form of the present invention forms an angle α to a perpendicular to the longitudinal axis. In certain embodiments, α is equal to 15 degrees. The external thread has a first pitch and a second pitch when the flexible shaft is flexed (corresponding to the compressed and tensioned portions of the shaft, respectively) and a third pitch when the flexible shaft is not flexed, with the second pitch being greater than the first pitch and the third pitch, and with the third pitch being greater than the first pitch. Stated another way, the flexible shaft of the present invention has a continuous pitch in a preflexed condition. When the shaft is flexed, the pitch on the tensioned portion of the implant increases, while the pitch on the compressed portion of the implant decreases.

The invention, in another form thereof, comprises a method of forming a curved, threaded hole into a bone and inserting a threaded, flexible implant into the curved, threaded hole. The method of this form of the present invention includes the steps of forming a curved hole with a first diameter into the bone; providing a first, threaded, flexible implant having the characteristics described in the preceding paragraph; inserting the first, threaded, flexible implant into the curved hole; and actuating the first, threaded, flexible implant such that the first, threaded, flexible implant taps the curved hole and forms a curved, threaded hole.

BRIEF DESCRIPTION OF THE DRAWINGS

The above-mentioned and other features and advantages of this invention, and the manner of attaining them, will become more apparent and the invention itself will be better understood by reference to the following description of an embodiment of the invention taken in conjunction with the accompanying drawings, wherein:

FIG. 1A is a cross-sectional view of the threaded, flexible implant of FIG. 1 taken along lines 1A-1A;

FIG. 1B is an enlarged, fragmentary view of the laser cut helix pattern which allows the implant of FIG. 1 to flex along its longitudinal axis;

Corresponding reference characters indicate corresponding parts throughout the several views. The exemplifications set out herein illustrate preferred embodiments of the invention, and such exemplifications are not to be construed as limiting the scope of the invention in any manner.

DETAILED DESCRIPTION

Figure 1:
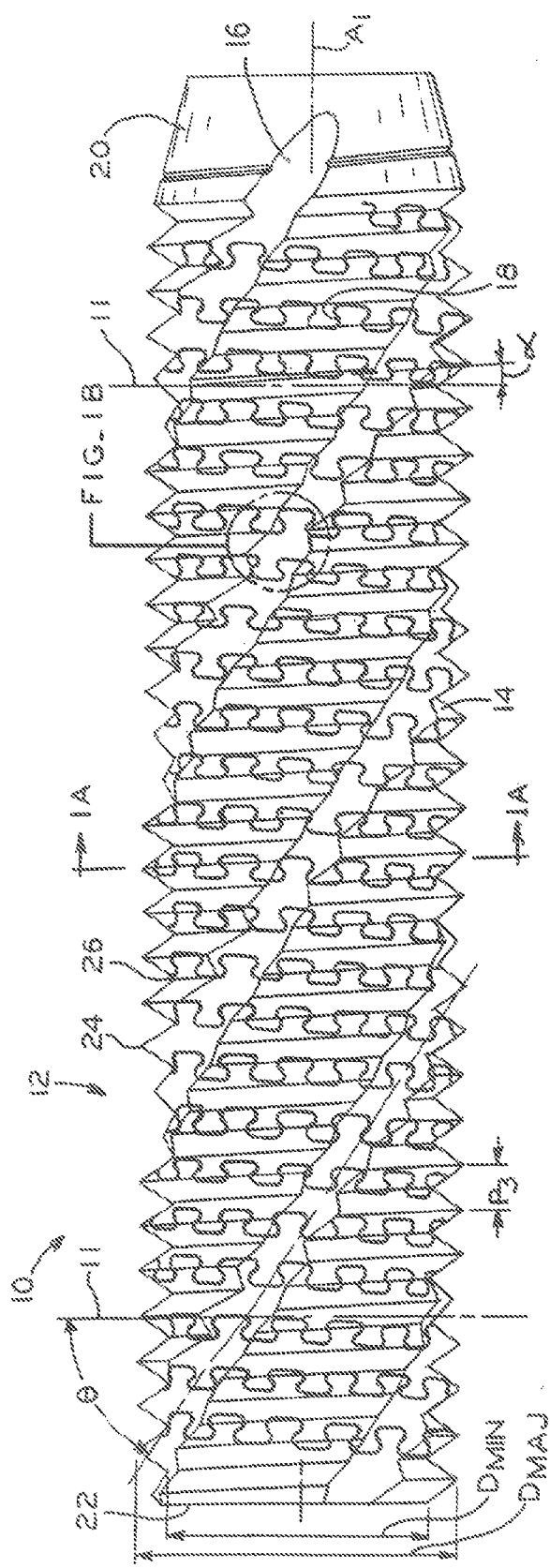
FIG. 1 is an elevational view of a threaded, flexible implant when it is not flexed.

FIG. 1 is an elevational view of threaded, flexible implant 10 when it is not flexed. In a flexed condition, longitudinal axis $A_1$ of threaded, flexible implant 10 is non-linear. Threaded, flexible implant 10 includes flexible shaft 12 with head portion 20 and tail portion 22, external thread 14, and laser cut spiral helix pattern 18. External thread 14 protrudes from flexible shaft 12 radially about longitudinal axis $A_1$. External thread 14 is positioned substantially perpendicular to longitudinal axis $A_1$. In an exemplary embodiment, external thread 14 is positioned a degrees from perpendicular 11 to longitudinal axis $A_1$. In one embodiment, α is equal to 15 degrees. In alternative embodiments, external thread 14 is positioned at about 10 degrees to about 20 degrees from perpendicular 11 to longitudinal axis $A_1$. When threaded, flexible implant 10 is not flexed, external thread 14 has pitch $P_3$. Pitch is the distance between adjacent crests 24 measured parallel to longitudinal axis $A_1$ of threaded, flexible implant 10. Pitch $P_3$ can be as great as about 0.1 inch, 0.2 inches, or 0.25 inches. Threaded, flexible implant 10 also includes major diameter $D_{maj}$ and minor diameter $D_{min}$, shown in FIGS. 1 and 1A. Major diameter $D_{maj}$ is the diameter of crest 24 of external thread 14. Minor diameter $D_{min}$ is the diameter of root 26 of external thread 14. Major diameter $D_{maj}$ and minor diameter $D_{min}$ can vary depending on the use intended for threaded, flexible implant 10. For example, when threaded, flexible implant 10 is to be implanted in femur 50 to reduce a femoral neck fracture, major diameter $D_{maj}$ can be about 0.75 inches and minor diameter $D_{min}$ can be about 0.642 inches.

Threaded, flexible implant 10 can be manufactured by first producing a threaded, cannulated shaft. This can be done by producing a cannulated shaft that includes walls thick enough to allow an external thread to be formed therein, followed by cutting a thread into the walls of the cannulated shaft. A slot in the form of a spiral helix is cut through the shaft wall to allow the shaft to flex. This can be done by any convenient means, such as computer controlled milling or cutting, wire electrical discharge machining, water jet machining, spark erosion machining, or laser cutting. Computer controlled laser cutting allows for a large variety of slot patterns to be produced, the ability to change the helix angle at any point along the shaft, variable slot width, and a high precision. A laser cut spiral helix pattern 18 is used in the exemplary embodiment. Laser cut spiral helix pattern 18 provides flexibility to flexible shaft 12 and, consequently, threaded, flexible implant 10. Spiral helix pattern 18 can be formed in accordance with the teachings of U.S. Pat. No. 6,053,922, the disclosure of which is hereby explicitly incorporated by reference herein. Threaded, flexible implant 10 can be made of any biocompatible materials, such as titanium, porous tantalum, SST, and cobalt chromium. In an alternative embodiment, if threaded, flexible implant 10 is made of a material other than porous tantalum, a porous metal coating, such as Cancellous-Structured Titanium (CSTi) porous coating, may be applied to external thread 14 to assist in osseointegration of threaded, flexible implant 10, which is described below.

Threaded, flexible implant 10 may also include flutes 16 that are formed helically about longitudinal axis $A_1$ in flexible shaft 12 and external thread 14. In an exemplary embodiment, flutes 16 are positioned at an angle θ from perpendicular 11 to longitudinal axis $A_1$ of flexible shaft 12, as shown in FIG. 1. In alternative embodiments, flutes 16 may be positioned at angles of about 75 degrees to about 80 degrees from perpendicular 11 to longitudinal axis $A_1$ of flexible shaft 12. Flutes 16 assist threaded, flexible implant 10 when threaded, flexible implant 10 is used to tap a bone. Flutes 16 may also assist in osseointegration of the implant by placing bone growth promoting material within flutes 16, as further discussed below.

Figure 2:
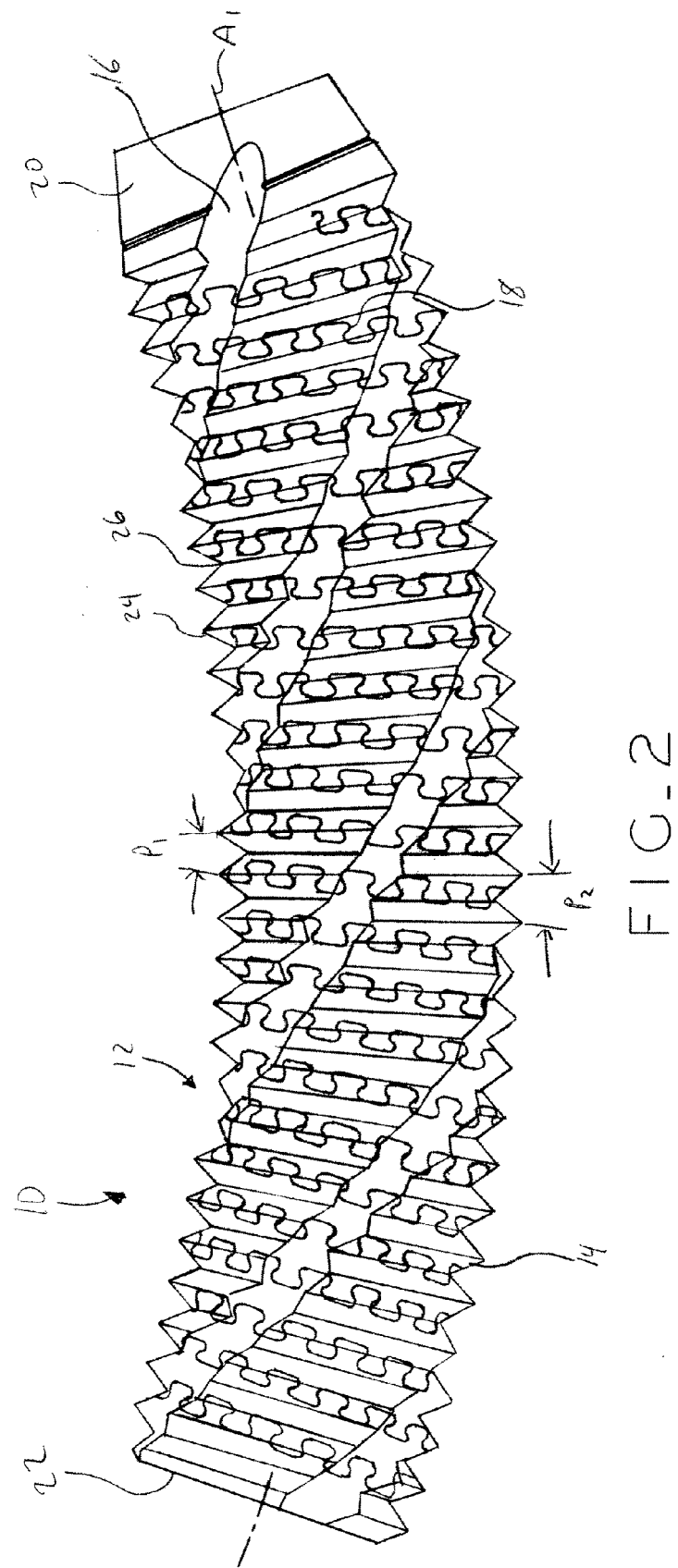
FIG. 2 is a radial, elevational view of the implant of FIG. 1 shown in a flexed condition.

FIG. 2 is an elevational view of threaded, flexible implant 10 when it is flexed. When threaded, flexible implant 10 is flexed, external thread 14 has pitch $P_1$ and pitch $P_2$. Pitch $P_2$ is greater than pitch $P_1$ and pitch $P_3$, seen in FIG. 1, and pitch $P_3$ is greater than pitch $P_1$. Pitch $P_1$ can be as great as about 0.5 inches, 0.1 inches, or 0.125 inches. Pitch $P_2$ can be as great as about 0.2 inches, 0.4 inches, or 0.5 inches. As threaded, flexible implant 10 is flexed, opposing sides are in tension and compression. As the surface of threaded, flexible implant 10 is in tension, the pitch expands, and as threaded, flexible implant 10 is in compression, the pitch contracts relative to its non-flexed condition.

Figure 3:
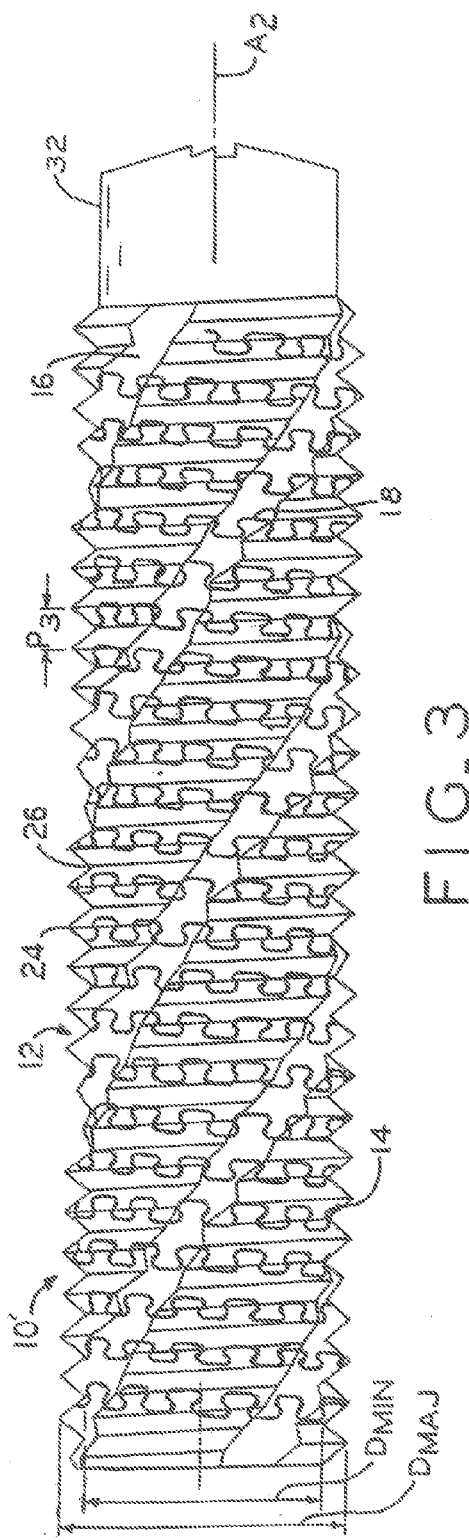
FIG. 3 is an elevational view of an alternative embodiment of the threaded, flexible implant of FIG. 1 when it is not flexed.
Figure 4:
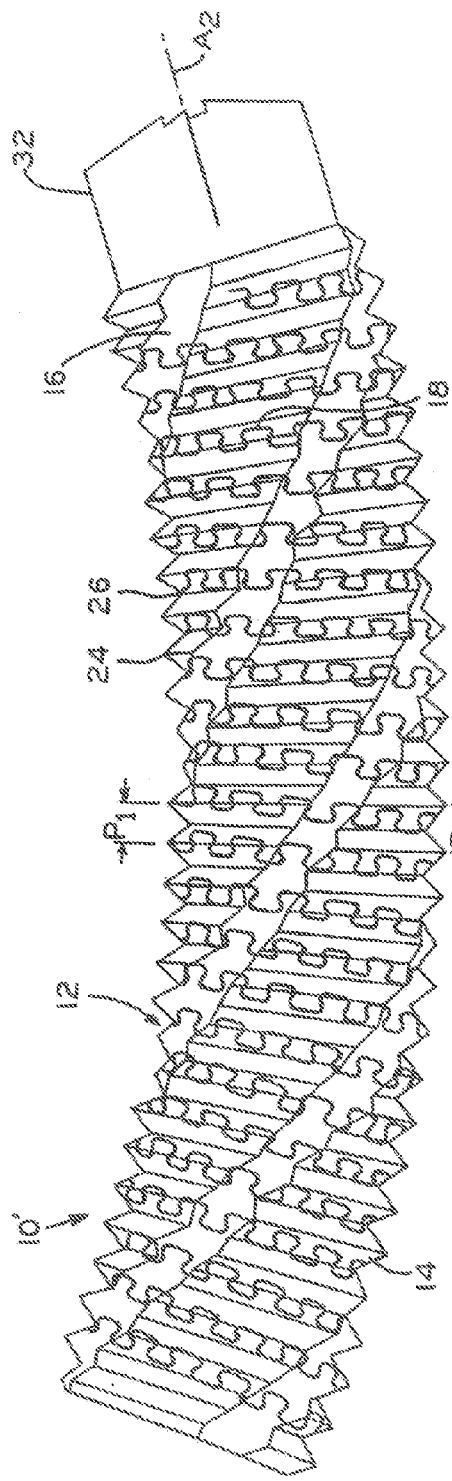
FIG. 4 is an elevational view of the threaded, flexible implant of FIG. 3 shown in a flexed condition.

Referring to FIGS. 3 and 4, an alternative embodiment of threaded, flexible implant 10 is shown. Threaded, flexible implant 10' is the same as threaded, flexible implant 10 with the addition of reamer 32.

Figure 7:
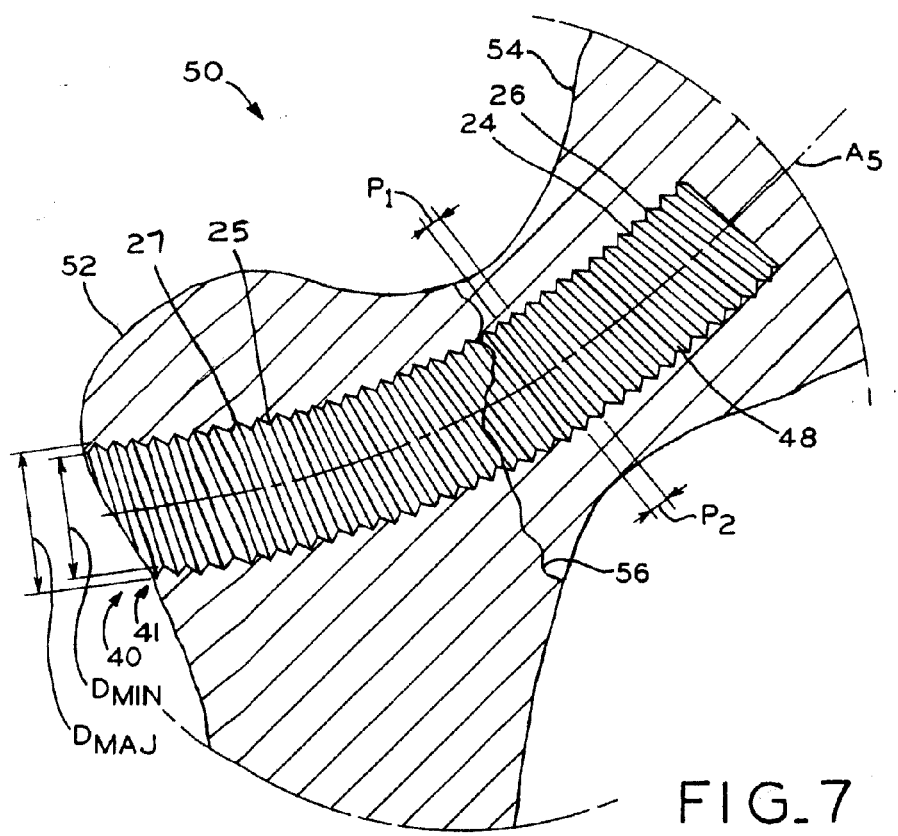
FIG. 7 is an elevational view of the threaded, curved hole of FIG. 5 formed in a femur.

FIG. 7 is an elevational view of threaded, curved hole 40. In an exemplary embodiment, threaded, curved hole 40 is formed in femur 50. Although threaded, curved hole 40 is described below as being formed in femur 50, threaded curved hole 40 may be formed in any other bone, such as a tibia or vertebra. Threaded, curved hole 40 includes internal thread 48 that protrude toward longitudinal axis $A_5$ of threaded, curved hole 40. Internal threads 48 have pitch $P_1$ and pitch $P_2$. Pitch $P_1$ and pitch $P_2$ of threaded, curved hole 40 are substantially equal to pitch $P_1$ and pitch $P_2$ of flexible, threaded implant 10, 10'. Pitch is the distance between adjacent roots 26 of internal thread 48 measured parallel to longitudinal axis $A_5$ of threaded, curved hole 40. Threaded, curved hole 40 also includes major diameter $D_{maj}$ and minor diameter $D_{min}$, shown in FIG. 7. Major diameter $D_{maj}$ is the diameter of root 26 of internal thread 48. Minor diameter $D_{min}$ is the diameter measured between diametrically opposed portions of crest 24 of internal thread 48. In an exemplary embodiment, $D_{maj}$ and $D_{min}$ remain constant throughout the length of curved, threaded hole 40. In an alternative embodiment, $D_{maj}$ and $D_{min}$ may vary over the length of curved, threaded hole 40. For example, $D_{maj}$ and $D_{min}$ start at their respective diameters and as curved, threaded hole 40 progresses into femur 50, $D_{maj}$ and $D_{min}$'s respective diameters could decrease to accommodate an implant which tapers from head to tail, i.e., it has a larger diameter at its head and a smaller diameter at its tail. In this instance, $D_{maj}$ and $D_{min}$ of threaded, flexible implant 10, 10' would correspond to the varying diameters of curved, threaded hole 40.

Figure 8:
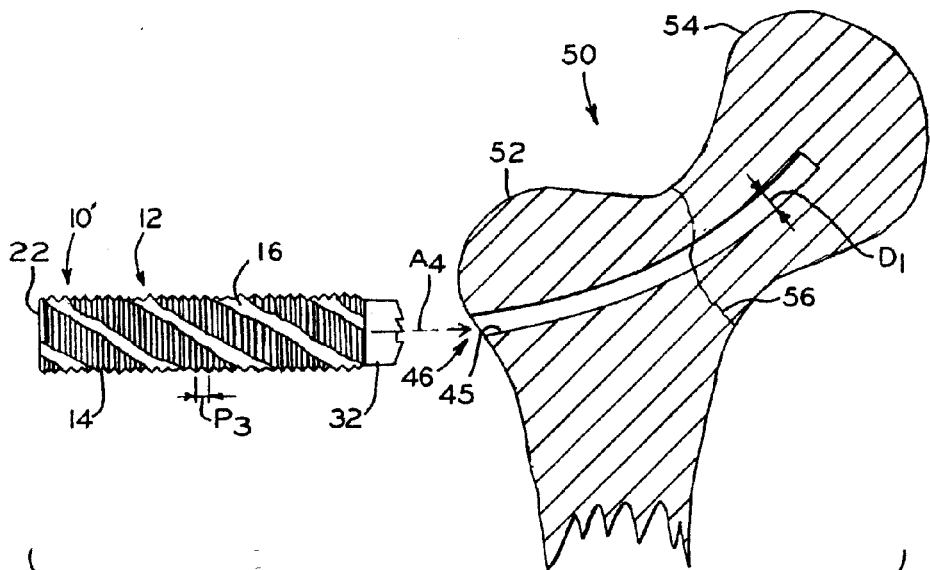
FIG. 8 is an elevational view of a drilled, curved hole in a femur with the threaded, flexible implant of FIG. 3 aligned for tapping the drilled, curved hole.

Referring to FIG. 8, curved hole 45 is formed in femur 50. Curved hole 45 is formed throughout first femoral portion 52 and second femoral portion 54, which are distinguished by fracture line 56 of femur 50. Curved hole 45 may be formed in femur 50 by any known surgical means, such as using a drill or the techniques shown in U.S. Pat. No. 6,447,514 assigned to the assignee of the present invention, the entire disclosure of which is hereby explicitly incorporated by reference. After formation, curved hole 45 will have first diameter $D_1$. Diameter $D_1$ will be sized dependent upon whether implant 10, or implant 10' will be utilized. Specifically, in the event that implant 10 will be utilized to tap hole 45, $D_1$ will be sized to be slightly smaller than $D_{min}$ of threaded, flexible implant 10. In the event that threaded, flexible implant 10' is utilized, $D_1$ can be significantly smaller than $D_{min}$ of threaded, flexible implant 10' because reamer 32 will be utilized to expand hole 45. In certain embodiments, hole 45 will be sized to accommodate a guide device such as a guide wire to guide insertion of flexible implant 10' to ream the femur while simultaneously tapping threaded hole 40.

Figure 5:
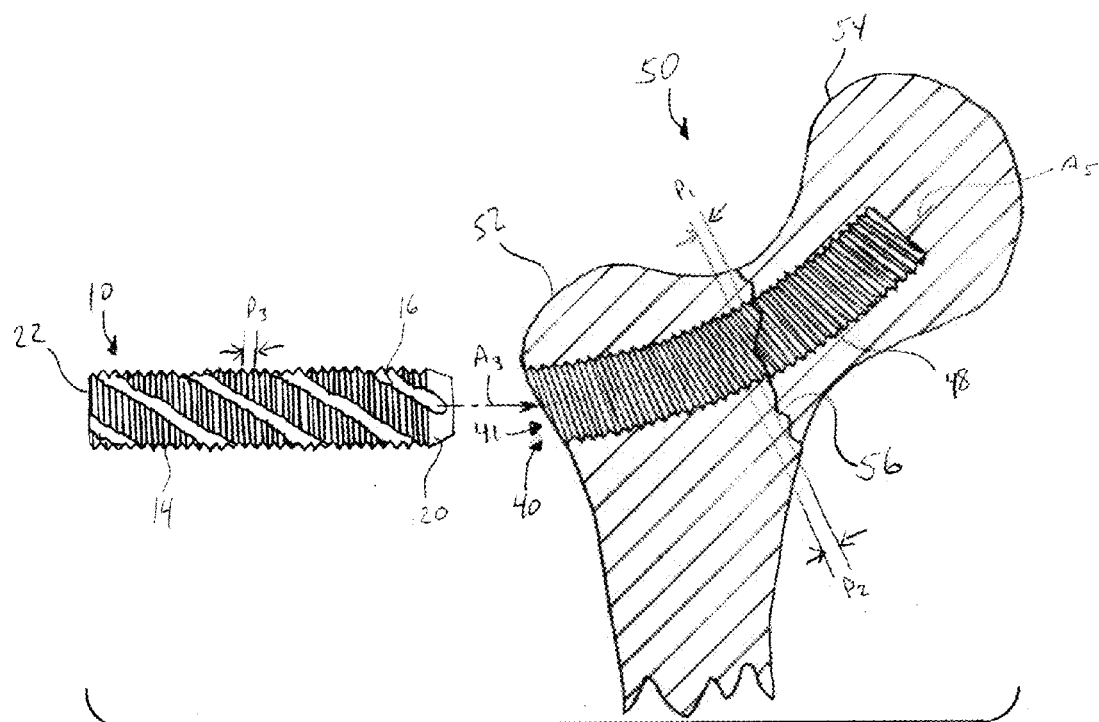
FIG. 5 is an elevational view of a threaded, curved hole formed in a femur with the implant of FIG. 1 aligned for insertion.
Figure 6:
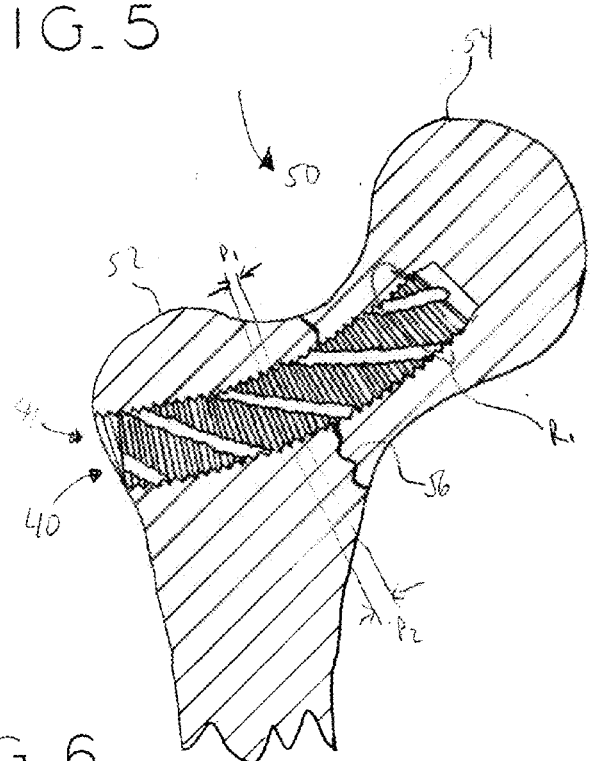
FIG. 6 is an elevational view of the implant of FIG. 1 inserted in and engaged with the threaded, curved hole of FIG. 5.

Referring now to FIGS. 5 and 6, a method of inserting threaded, flexible implant 10 into threaded, curved hole 40 is illustrated. Threaded, flexible implant 10 is aligned with curved, threaded hole 40 and an end of threaded, flexible implant 10 is inserted into opening 41 of curved, threaded hole 40 along arrow $A_3$, seen in FIG. 5. External thread 14 of threaded, flexible implant 10 engages internal thread 48 of curved, threaded hole 40 and threaded, flexible implant 10 is actuated along arrow $R_1$ such that external thread 14 of threaded, flexible implant 10 engages internal thread 48 of curved, threaded hole 40, as seen in FIG. 6. Threaded, flexible implant 10 may be actuated by hand, mechanical device or any other means known in the art. In an alternative embodiment, threaded, flexible implant 10 may be actuated in the opposite direction of arrow $R_1$.

The different thread pitches of threaded, flexible implant 10 and corresponding thread pitches $P_1$ and $P_2$ of curved, threaded hole 40 allow for tight integration of the two thread sets together. As threaded, flexible implant 10 is actuated and flexed while inserted in curved, threaded hole 40, external thread 14 is engaged with internal thread 48. As this occurs, pitch $P_1$ is present along a portion of threaded, flexible implant 10 where external thread 14 has a shorter distance to travel within curved, threaded hole 40. At the same time, pitch $P_2$ is present along a portion of threaded, flexible implant 10 where external thread 14 has a greater distance to travel within curved, threaded hole 40. As threaded, flexible implant 10 rotates 180 degrees along its longitudinal axis $A_1$, pitch $P_1$ will become pitch $P_2$, and vice versa. As head portion 20 of threaded, flexible implant 10 reaches the end of curved, threaded hole 40, i.e., internal threads 48 no longer exist inside of curved, threaded hole 40, pitch $P_1$ and pitch $P_2$ of threaded, flexible implant 10 are aligned with pitch $P_1$ and pitch $P_2$ of curved, threaded hole 40. This is beneficial in keeping threaded, flexible implant 10 fixed in position in femur 50, and is also beneficial to keep threaded, flexible implant 10 fixed in position during the osseointegration process.

Osseointegration is the firm anchoring, or integration, of a surgical implant, such as threaded, flexible implant 10, by the growth of bone in and around the implant with fibrous tissue formation at the interface between the implant and the bone. The osseointegration process acts as a second layer of fixation of threaded, flexible implant 10 to femur 50. External thread 14 and flutes 16 provide a greater amount of surface area which leads to more contact at the interface between threaded, flexible implant 10 and femur 50. As threaded, flexible implant 10 is engaged with curved, threaded hole 40, small shavings of bone are positioned between external thread 14 and flutes 16, which is beneficial in the osseointegration process. When implant 10' is utilized, the reaming and tapping process positions bone fragments within the flutes 16. If implant 10' is left in position after reaming and tapping the bone in which it is implanted, these bone fragments facilitate bone ingrowth into the flutes of implant 10' to facilitate its securement within the bone. In the event that implant 10 is positioned within an already tapped hole in a bone, bone fragments may be packed within flutes 16 to similarly facilitate osseointegration of implant 10.

FIG. 6 illustrates the final insertion and engagement of threaded, flexible implant 10 into curved, threaded hole 40. Once flexible implant 10, 10' is finally seated within the bone, its longitudinal cannula may be filled with a flexible core to provide additional rigidity to the implant. In certain embodiments, the core may be formed from a guide wire having an outer diameter close in size to the inner diameter of the implant cannula. This configuration is particularly useful when implant 10' is utilized to ream and tap the femur and is thereafter left in place as a final implant. In this embodiment, threaded, flexible implant 10 connects first femoral portion 52 and second femoral portion 54 along fracture line 56. As mentioned above, the methods and apparatuses of the present invention are not limited to use in reducing a femoral neck fracture. Some other uses include threaded, flexible implant 10 with a prosthetic femoral head implant connected thereto. Curved, threaded hole 40 and threaded, flexible implant 10 can be formed and engaged as described above with the addition of a femoral head implant connected to threaded, flexible implant 10.

Threaded, flexible implant 10 may also be utilized as a spinal fixation device. Formation of curved, threaded hole 40 can begin axially and follow along the curvature of the vertebra while threaded, flexible implant 10 can be inserted and engaged along the same path. This use allows for the avoidance of nerves and provides better fixation due to a longer implant throughout the vertebra.

Another use is to utilize the present invention when fixating a tibial tray to a tibia. This would assist in further fixation for an apparatus and method shown in U.S. Provisional Patent Application No. 60/586,706, the entire disclosure of which is hereby explicitly incorporated by reference. The present invention would allow the channel portion of the tibial tray to be stronger in that the inner tibial channel would be threaded, allowing for further fixation of the tibial tray to the tibia.

While this invention has been described as having a preferred design, the present invention can be further modified within the spirit and scope of this disclosure. This application is therefore intended to cover any variations, uses, or adaptations of the invention using its general principles. Further, this application is intended to cover such departures from the present disclosure as come within known or customary practice in the art to which this invention pertains and which fall within the limits of the appended claims.

What is claimed is:

1. A threaded, flexible implant, comprising:
a biocompatible flexible shaft including a head portion and a tail portion, the biocompatible flexible shaft extending along a longitudinal axis; an external thread protruding radially from said flexible shaft helically about said longitudinal axis from said head portion to said tail portion, said external thread forming an angle α to a perpendicular to said longitudinal axis, said external thread having a first pitch and a second pitch when said flexible shaft is flexed, and a third pitch when said flexible shaft is not flexed, wherein said second pitch is greater than said first pitch and said third pitch, and said third pitch is greater than said first pitch, said shaft having a flute formed helically about said longitudinal axis of said flexible shaft, said flute intersecting said external thread, said flute extending from said head portion to said tail portion; and
a bone growth promoting material positioned in said flute to promote osseointegration of the implant with a bone.

2. The threaded, flexible implant of claim 1, wherein said flexible shaft comprises a hollow core.

3. The threaded, flexible implant of claim 2, wherein said flexible shaft further comprises a continuous cut-out from an outer diameter of said shaft to an inner diameter of said shaft, said cut-out defining the hollow core of said shaft.

4. The threaded, flexible implant of claim 1, wherein said flexible shaft comprises a solid core.

5. The threaded, flexible implant of claim 1, further comprising a reamer connected to said head portion of said flexible shaft, said reamer being rotationally fixed relative to the flexible shaft.

6. The threaded, flexible implant of claim 5, wherein said reamer is configured to position said bone growth promoting material in said flute while said threaded, flexible implant is being threaded into the bone.

7. The threaded, flexible implant of claim 1, wherein said angle α equals about 15 degrees.

8. The threaded, flexible implant of claim 1, wherein said flexible shaft comprises a cannulated flexible shaft having an internal wall, said internal wall defining a cannula through a length of said shaft.

9. The threaded, flexible implant of claim 1, wherein said flute forms an angle of about 75 degrees to a perpendicular to the longitudinal axis of the flexible shaft.

10. The threaded, flexible implant of claim 1, wherein said bone growth promoting material comprises bone fragments.

11. A threaded, flexible implant, comprising:
a biocompatible flexible shaft including a longitudinal axis, an external thread protruding radially from said flexible shaft helically about said longitudinal axis, said external thread forming an angle α to a perpendicular to said longitudinal axis, said external thread having a first pitch and a second pitch when said flexible shaft is flexed, and a third pitch when said flexible shaft is not flexed, wherein said second pitch is greater than said first pitch and said third pitch, and said third pitch is greater than said first pitch, said flexible shaft comprising a cannulated flexible shaft having an internal wall, said internal wall defining a cannula through a length of said shaft;

a core formed from a guide wire having an outer diameter sized to selectively fit within said internal wall of said cannulated flexible shaft; and a reamer fixedly connected to a proximal end of said flexible shaft, wherein a flute is formed helically about said longitudinal axis of said flexible shaft, said flute intersecting said external thread, said flute and said external thread extending from a head portion to a tail portion of said flexible shaft.

12. The threaded, flexible implant of claim 11, further comprising a bone growth promoting material positioned in said flute to promote osseointegration of the implant with a bone.

13. The treaded, flexible implant of claim 12, wherein said reamer is configured to position said bone growth promoting material in said flute while said threaded, flexible implant is being threaded into the bone.

14. A threaded, flexible implant, comprising:

a biocompatible flexible shaft including a head portion and a tail portion, the biocompatible flexible shaft extending along a longitudinal axis, said shaft having a slot extending along said longitudinal axis, wherein said slot provides flexibility to said shaft; and an external thread protruding radially from said flexible shaft helically about said longitudinal axis from said head portion to said tail portion, said external thread intersecting said slot and forming an angle α to a perpendicular to said longitudinal axis, said external thread having a first pitch and a second pitch when said flexible shaft is flexed and a third pitch when said flexible shaft is not flexed, wherein said second pitch is greater than said first pitch and said third pitch, and said third pitch is greater than said first pitch, said shaft having a flute formed helically about said longitudinal axis of said flexible shaft and extending from said head portion to said tail portion, said flute intersecting said external thread and said slot, said flexible shaft comprising a cannulated flexible shaft having an internal wall, said internal wall defining a cannula through a length of said shaft;

a reamer connected to said head portion to position a bone growth promoting material in said flute to promote osseointegration of the implant with a bone; and a core formed from a guide wire having an outer diameter sized to selectively fit within said internal wall of said cannulated flexible shaft.

15. The threaded, flexible implant of claim 14 wherein said slot extends from an external wall of said shaft through said cannulated flexible shaft.

16. The threaded, flexible implant of claim 14, wherein said reamer is fixedly connected to said head portion of said flexible shaft.

17. The threaded, flexible implant of claim 16, wherein said reamer is configured to position said bone growth promoting material in said flute while said threaded, flexible implant is being threaded into the bone.

18. The threaded, flexible implant of claim 14, wherein said angle α equals about 15 degrees.

19. The threaded, flexible implant of claim 14, wherein said flute forms an angle of about 75 degrees to a perpendicular to the longitudinal axis of the flexible shaft.

* * * * *